(12) United States Patent
Schauer

(10) Patent No.: US 7,835,007 B2
(45) Date of Patent: Nov. 16, 2010

(54) METHODS AND APPARATUS FOR IDENTIFYING THIN FILMS ON A SUBSTRATE

(75) Inventor: Ronald Vern Schauer, Gilroy, CA (US)

(73) Assignee: Applied Materials, Inc., Santa Clara, CA (US)

( * ) Notice: Subject to any disclaimer, the term of this patent is extended or adjusted under 35 U.S.C. 154(b) by 301 days.

(21) Appl. No.: 12/184,673

(22) Filed: Aug. 1, 2008

(65) Prior Publication Data

US 2009/0033941 A1 Feb. 5, 2009

Related U.S. Application Data

(60) Provisional application No. 60/953,212, filed on Aug. 1, 2007.

(51) Int. Cl.
*G01N 21/47* (2006.01)
*G01N 21/55* (2006.01)

(52) U.S. Cl. .................................. 356/446; 356/448

(58) Field of Classification Search ......... 356/445–448, 356/450–458
See application file for complete search history.

(56) References Cited

U.S. PATENT DOCUMENTS

| | | | |
|---|---|---|---|
| 4,048,510 A * | 9/1977 | Clarke et al. ............ 250/559.48 |
| 5,233,191 A * | 8/1993 | Noguchi et al. ................. 850/1 |
| 5,898,181 A | 4/1999 | Vurens |
| 6,042,995 A * | 3/2000 | White ......................... 430/311 |
| 6,630,995 B1 * | 10/2003 | Hunter .................... 356/237.5 |
| 7,417,724 B1 * | 8/2008 | Sullivan et al. .......... 356/237.2 |
| 2002/0015146 A1 | 2/2002 | Meeks et al. |

OTHER PUBLICATIONS

International Search Report and Written Opinion of International Application No. PCT/US08/09277 (11732-PCT) mailed Nov. 13, 2008.
International Preliminary Report on Patentability and Written Opinion of International Application No. PCT/US08/09277 (11732-PCT) mailed Feb. 11, 2010.

* cited by examiner

*Primary Examiner*—Gregory J Toatley, Jr.
*Assistant Examiner*—Jarreas C Underwood
(74) *Attorney, Agent, or Firm*—Dugan & Dugan, PC

(57) ABSTRACT

The present invention provides systems, apparatus and methods for detecting a film in an electronic device disposed in an electronic device processing tool. The invention includes a mounting member adapted to couple the apparatus to a view port of the electronic device processing tool, an optical energy source disposed within the mounting member and adapted to illuminate the electronic device within the electronic device processing tool, an optical system adapted to pass wavelengths indicative of a presence of the film, and an optical detector positioned to receive optical energy reflected from the substrate and passing through the optical system adapted to detect a presence or absence of the film. Numerous other features are disclosed.

18 Claims, 11 Drawing Sheets

METHODS AND APPARATUS FOR IDENTIFYING THIN FILMS ON A SUBSTRATE

RELATED APPLICATIONS

The present application claims priority to U.S. Provisional Application No. 60/953,212 filed Aug. 1, 2007 entitled "METHODS AND APPARATUS FOR IDENTIFYING THIN FILMS ON A SUBSTRATE" which is hereby incorporated herein by reference for all purposes.

FIELD OF THE INVENTION

The present invention relates to electronic device manufacturing and, more particularly, to methods and apparatus for identifying thin films on a substrate disposed in a chamber.

BACKGROUND OF THE INVENTION

In electronic device fabrication processes, it is often important to be able to detect the layers and or films (e.g., a copper layer) that have been deposited or otherwise positioned on a substrate, while the substrate is being operated upon in a processing tool. For example, some film materials may not be compatible with some chambers or processes and bringing a substrate into an incompatible chamber may damage the chamber. Conventional devices for performing film detection suffer from a number of drawbacks in terms of complexity, cost, time, and ease of use. Typically, conventional devices require the substrate to be removed from the processing tool to be analyzed. It would therefore be desirable to provide a film detection device that provides a combination of functionality, utility, form factor, application, low cost and simplicity of setup and operation that can also enable film detection within a processing tool.

SUMMARY OF THE INVENTION

In some aspects of the present invention, a method for detecting a film is provided. A method of detecting a film in an electronic device disposed an electronic device processing tool includes coupling a mounting member of a film detection apparatus to a view port of the electronic device processing tool; illuminating the electronic device within the electronic device processing tool using an optical energy source disposed within the mounting member; passing wavelengths indicative of a presence of the film via an optical system coupled to the mounting member; receiving optical energy reflected from the substrate; and detecting a presence or absence of the film based on the received optical energy using an optical detector.

In another aspect of the present invention, an apparatus for detecting a film is provided. The invention includes a mounting member adapted to couple the apparatus to a view port of the electronic device processing tool, an optical energy source disposed within the mounting member and adapted to illuminate the electronic device within the electronic device processing tool, an optical system adapted to pass wavelengths indicative of a presence of the film, and an optical detector positioned to receive optical energy reflected from the substrate and passing through the optical system adapted to detect a presence or absence of the film.

In yet another aspect of the present invention, a system for detecting a film is provided. The system for detecting a film in an electronic device includes an electronic device processing tool; a mounting member adapted to couple to a view port of the electronic device processing tool; an optical energy source disposed within the mounting member and adapted to illuminate the electronic device within the electronic device processing tool; an optical system coupled to the mounting member and adapted to pass wavelengths indicative of a presence of the film; and an optical detector positioned to receive optical energy reflected from the substrate and passing through the optical system adapted to detect a presence or absence of the film.

Other features and aspects of the present invention will become more fully apparent from the following detailed description, the appended claims, and the accompanying drawings.

DETAILED DESCRIPTION

Figure 1:
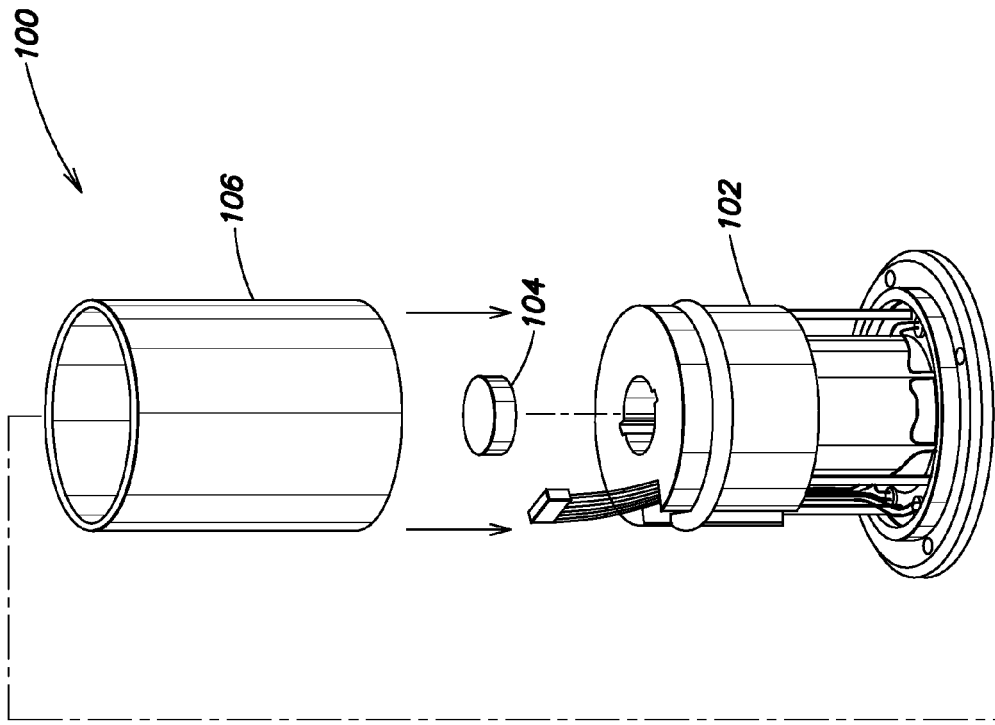
FIG. 1 depicts an exploded perspective view of a first example apparatus embodiment of the present invention.
Figure 1:
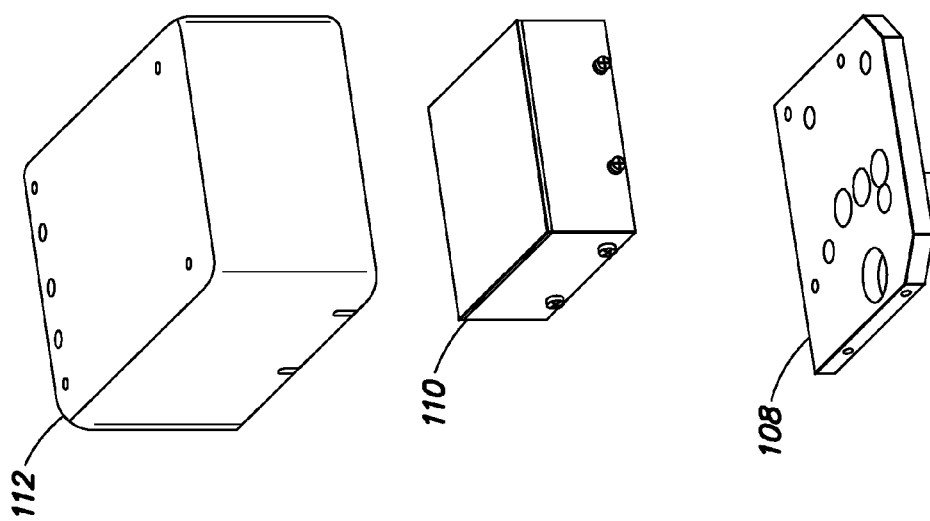

According to the present invention, an apparatus for detecting a film in or on an electronic device ('film detection apparatus') is provided which includes a number of useful features. The accompanying drawings depict features and operation of one or more embodiments of the film detection apparatus according to the invention.

In one or more embodiments, the film detection apparatus is provided with a unitary mounting member adapted to easily couple to viewing ports of one or more electronic device processing tools (e.g., transfer chambers, processing chambers, etc.), such as the Centura® or Endura® processing tools manufactured by Applied Materials Inc. of Santa Clara, Calif. The mounting member may be designed to prevent reflections off the window of a viewing port of the light (e.g., optical spectrum energy) used by the film detection apparatus which otherwise may affect the film detection process. To detect thin films which may be positioned beneath several other layers on a substrate in a processing tool, the film detection apparatus includes one or more optical spectrum energy sources ('light sources') which may range from infrared (about 1500 nm)

through far ultraviolet (about 150 nm), one or more optical detectors adapted to detect the wavelength or wavelengths that the light sources emit and/or secondary emissions from the substrate, one or more diffusers, and one or more narrow-band filters adapted for sensitivity to the particular film being detected. The filter wavelengths may be different from the wavelengths emitted by the light sources since in some cases secondary or shifted emissions are reflected from the film on the substrate. Selection of suitable filters removes the need for special alignments. To assist in detection, the film detection apparatus may also include features that are adapted to block ambient light sources to reduce background signals. Additional devices to modify the optical path so as to reduce effect of pattern geometry on substrates may also be included. Such devices may include but are not limited to, lenses, windows, collimators and diffusers. Automated (e.g., via control software) and/or manual mechanisms for controlling the intensity of energy emitted from the light sources and the gain of the optical detectors during operations may be provided.

The film detection apparatus also includes a number of features that improve safety and reliability. For example, in some embodiments, the film detection apparatus includes an enclosure having shielding designed to limit and/or prevent unintentional operator exposure to optical energy sources and to provide couplings in a manner that avoids disconnection of power when opening the enclosure. In one or more embodiments, the apparatus may include safety interlock switches that prevent unintentional exposure to optical energies outside the eye-safe wavelength range.

Stable light sources, such as solid state light sources that emit at a fixed wavelength may be used singly or in combination as may be appropriate. Such light sources may be chose to long and stable service (e.g., up to 500 to 1000 times the service of light sources used in conventional film detection devices). The light sources may be designed to turn on in an extremely short time, so that they can be energized only for the brief time required to take a measurement and make a determination (requiring no repeated calibrations), resulting in appreciable energy savings. The extremely rapid turn-on and brief use of the light sources promotes safety. For example, where ultra-violet or infrared sources are employed, exposure to which for certain periods may be hazardous, the light source is energized only for brief periods while other safety criteria (e.g., shielding, enclosure closed) are met.

In addition, in some embodiments, the film detection apparatus may be employed as a presence sensor to determine whether a substrate has been placed within processing equipment. The presence sensor may comprise a separate optical light source and optical detector assembly.

The present invention also provides a control system and/or software adapted to interface with and control the film detection apparatus according to the invention. The control system may include one or more logic circuits adapted to: perform and record calibrations of the film detection apparatus; determine the presence or absence of a substrate; couple to other control systems in a fabrication facility.

In some embodiments, the present invention may utilize a mounting means that is specific to commercially available (e.g., Applied Materials' Centura® and Endura®) transfer chamber lid viewing window ports (a simple bolt-on). This mounting means is conceived to be easily adaptable to other types and styles of equipment.

The present invention is designed to normally block ambient light sources for process uniformity. This is an inherent part of the design that does not require additional engineering methods or solutions.

The present invention is designed to limit or prevent unintentional operator exposure to the optical energy source(s). Other features include built-in safety cutoff switches (as necessary) and engineering safety solutions such as designing the connecting cabling in a manner that prevents enclosure opening without disconnection of power. Singly and in combination, these enhance operator and installer safety. Prior art equipment often requires complex or awkward safety shielding to achieve the same goal.

The present invention is designed as a compact unitary (modular) bolt-on assembly as opposed to prior art that is assembled in place from various parts and whose components may be scattered about the system.

The present invention is designed to be capable of interfacing with commercially available systems such as the Centura® and Endura® substrate processing systems (e.g., plug and play). The interface is designed to be very simple in nature so as to enhance flexibility, however it may be readily adapted to other platforms and systems. The present invention may also contain a more complex system interface (such as serial data transfer) as necessary, but the presence and use of such interfaces is not required for operation.

As opposed to spectrographs and spectrometers which are better suited to analytical tasks and complex analysis, the present invention is designed to be task-specific. Spectrographs and spectroscopes may be utilized to help determine the sensing ranges for which this device is adapted, however, they are not required in any form whatsoever for the installation or usage of the present invention once configured.

Configuration of the present invention during manufacture is simple and highly tolerant of modest skill sets. The device is tuned to the desired wavelength band or bands using standard commercial narrow band optical filter(s) and light source selections. Very few if any special alignments are required.

Solid state light sources and/or other fixed wavelength energy sources may be used singly or in combination as may be appropriate. These are chosen for long and stable service (500×-1000× the service life of the prior art sources). These devices do not degrade noticeably over their normal service lifetimes and so may be considered permanent. The preferred light sources are also "instant on", requiring no appreciable warm up periods. This means that they may be energized for only the brief time required to take a measurement and make a decision. For this reason the light sources do not require repeated recalibrations and will have further enhanced service lifetimes. Moreover the light sources are approximately 0.05% of the cost of prior art sources, produce no acoustic noise in operation, and use less than 1% as much energy to operate.

The instant on light sources utilized by the present invention are also a safety enhancement. Where ultra-violet or infrared sources are utilized, the sources will only be energized for brief periods of time and only if all safety interlock criteria are met.

In-situ calibration of the present invention is accomplished by activating the system to scan a calibration substrate as the calibration substrate is moved along a simple substrate motion sequence or profile (e.g., moving the substrate in a horizontal pattern that allows portions of the major surface of the substrate to pass under the system). This is completely different than prior art sensors that use spectrographs and spectroscopes or other more complex means. The present invention only takes 1% to 2% of the time and effort compared to prior art tools, with a correspondingly lower required skill level from both installers and operators.

The present invention may be considered to be a "process excursion" sensing device. Prior art tools were designed as a broad based "analytical instruments" and while such prior art tools may be adapted to perform a similar function, these tools have proven to be expensive, difficult, and time consuming to configure, install, use, and maintain.

No special windows, fiber optics, vacuum seals or any other such items are required for installation and usage. The pre-existing vacuum seals are not breached during installation or usage. This allows very rapid installation and service to be performed without changes to substrate fabrication processes or chambers.

The present invention in some embodiments includes an optical spectrum energy source or multiplicity of sources, which may range in wavelength from far infrared (~1500 nanometers) through far ultraviolet (~150 nanometers) inclusive, as necessary for sensing reliability.

Optional integral safety interlock switches may be included to prevent unintentional exposure of technicians and operators to optical energies outside the eye-safe wavelength range, or which may be merely uncomfortable to view for long periods of time. Optional eye-safe view port windows may be present as required.

Optional separate substrate presence optical emitter and detector devices may be included. This function may also be performed by the main film sensor in most instances. The present invention may include an automated or manual means to control the intensity of the optical energy source during service operations and as part of a semi-automated calibration sequence. The present invention may include an automated or manual means to control the gain or sensitivity of the sensing device during service operations and as part of a semi-automated calibration sequence.

The present invention may include an optical sensor or group of sensors capable of detecting the wavelength or wavelengths that the optical energy sources emit, and/or secondary emissions from the substrate being sensed.

The present invention may include one or more optical filters that are specified for sensitivity with the semiconductor substrate film type being detected. Note that the filter wavelengths may or may not be the same as the incorporated optical energy sources, because in some cases secondary or shifted emissions or combinations thereof are to be detected, even though the light energy source may itself be monochromatic. The mountings for the optical filters are designed such that they may be easily reconfigured as necessary.

The present invention may include an optical path that limits the sensor or sensors to a certain area or range. Such a path may contain lenses, windows, collimators, diffusers, and other devices to enhance this function and also to help negate the effects of pattern geometry on the substrates being sensed.

The present invention may include a means of interfacing between the optical sensor or sensors and the host equipment. The present invention may include a logic circuit capable of performing and recording calibrations of the assembly, both in production and in service conditions. The present invention may include a logic circuit that is capable of making decisions about the substrate film being sensed based upon the calibrations. The present invention may include a logic circuit that is capable of determining the presence or absence of substrates in the field of view of the sensing device or devices, including instances where substrate blade face openings are not provided. The present invention may include a logic circuit that contains means to perform semi-automatic calibration routines. It may also include means to be manually calibrated as necessary. The present invention may include a logic circuit that contains means to connect to substrate processing equipment control logic in a plug-and-play manner. This means may be readily adaptable to other systems and equipment as well.

The present invention may include a mechanical structure and optical paths capable of operating without restricting the motions of a substrate handling robot blade and supporting arms. The present invention may include a mounting geometry that prevents first and second surface reflections from the vacuum chamber window from adversely affecting the returned sensing optical signals. The present invention may include an optional integral reference target surface for self-calibration or a standardized target substrate to help effect said calibration.

A mechanical array device to contain and align the optical energy sources and to direct their output to a convergent point or controlled illumination field area.

The present invention in other embodiments may include the features of the invention as described above except more than one wavelength of optical spectrum energy source may be present (polychromatic aggregate source) as required. In some embodiments, one or more optical filters specified for sensitivity with the semiconductor substrate film type being detected. Note that the filter wavelengths may or may not be the same as the incorporated optical energy sources, because in some cases secondary or shifted emissions or combinations thereof are to be detected. In some embodiments, the multiplicity of optical wavelengths in the energy source may be simultaneous, sequenced, or selectively enabled depending upon need.

The present invention in another embodiment includes the invention of the above embodiments except optional magnetic field and radio frequency field sensing means are used in conjunction with the optical spectrum sensors. Where applicable, this may take the form of sensing coils mounted in close proximity to the substrate being examined and in some cases mechanically replacing the pre-existing chamber view window and mount.

The present invention in another embodiment includes the invention as described above except a coaxial light source which is effected by means of beam splitters, multiple-strand fiber optics, mirrors, or similar means is used. The coaxial light source may be used in lieu of the convergent light source. The coaxial light source may be used in conjunction with the convergent light source and may be used separately, simultaneously, or in combination to effect measurements.

Turning to FIG. 1, a specific example embodiment of the present invention is now described for the purposes of illustration. An exploded perspective view drawing depicts the example film detection apparatus 100 embodiment of the present invention. The example apparatus 100 includes an optical energy supply base assembly 102 that is adapted to support a top diffuser 104 and to be surrounded by an outer tube housing 106. The outer tube housing 106 also couples to a base plate 108 which supports an optical sensor assembly 110 and is surrounded by a shield housing 112.

The apparatus 100 is adapted to easily be attached to a processing tool (not shown) (e.g., a transfer chamber, a processing chamber, etc.) at a view port (not shown) of the processing tool. When attached, the apparatus is disposed to both illuminate and scan substrates within the processing tool through the view port. The lower portion of the optical energy supply base assembly 102 is shaped to fit within a frame (not shown) of the view port so that the bottom annular surface 202 (FIG. 2) of the assembly 102 sits flush with the transparent material (e.g., quartz window) of the view port and the outer flange edge 204 (FIG. 2) of the assembly 102 overhangs the frame of the view port to facilitate attachment (e.g., via bolts).

In some embodiments, the structural components of the apparatus 100 (e.g., the housings, base plate, etc.) may be formed from aluminum or any other practicable material.

The top diffuser 104 may be made of opal glass which is translucent but not transparent to optical energy. In some embodiments, a thin layer of opal glass (e.g., approximately 0.05 to approximately 0.3 mm thick and preferably approximately 0.1 mm thick) may be fused to a thicker clear piece of glass (e.g., approximately 6 mm thick) to form the top diffuser 104. The top diffuser 104 is disposed horizontally and in line with a central optical energy path that extends up from the view port of the processing tool, through the center of the optical energy supply base assembly 102, through the top diffuser 104, through an aperture in the base plate 108 (which may include one or more optical filters), and into the optical sensor assembly 110.

The outer tube housing 106 (along with the shield housing 112) is adapted to shield the optical energy supply base assembly 102 and to both prevent ambient light from entering the optical sensor assembly 110 as well protect operators from exposure to optical energy from the optical energy supply base assembly 102. Although the outer tube housing 106 is depicted as a tube, other shapes may be used.

The optical sensor assembly 110 is disposed above and supported by the base plate 108. The optical sensor assembly 110 is adapted to generate a signal indicative of the detection of a particular target range of energy wavelengths in response to receiving optical energy that is inclusive of the target range from the processing tool. In some embodiments for example, a Model PM100-V detector assembly, commercially available from Verity Instruments, Inc. of Carrollton, Tex., may be used as the optical sensor assembly 110. In such embodiments, the sensor assembly 110 may be embodied as a replaceable or upgradeable modular component that is separate from the rest of the circuitry of the apparatus 100. In other embodiments, for example as described below with respect to FIG. 13, the optical sensor assembly 110 may be embodied as an integral component of a controller of the apparatus 100. In some embodiments, the base plate 108 may also support a optical bandpass filter 306 (FIG. 3) in or adjacent the aperture between the optical sensor assembly 110 and the top diffuser 104. Additional and other types of filters, as discussed above, may be used.

The shield housing 112 covers the top of the apparatus 100 and encloses the optical sensor assembly 110 as well as the controller and other circuitry (not visible in FIG. 1) of the apparatus 100. As with the outer tube housing 106, the shield housing 112 is adapted to prevent ambient light from entering the optical sensor assembly 110 as well protect operators from exposure to optical energy from the optical energy supply base assembly 102.

Figure 2:
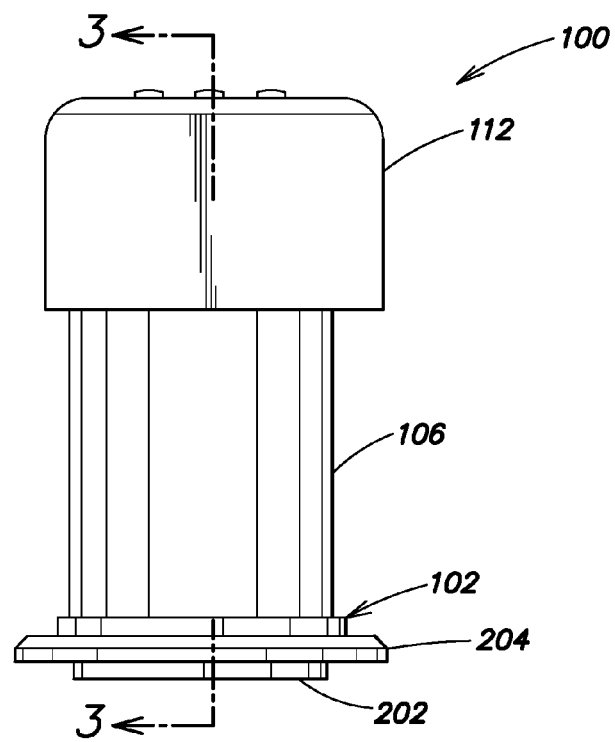
FIG. 2 depicts a side view of the example apparatus embodiment of FIG. 1.

Turning to FIG. 2, a side view of the apparatus 100 is depicted that illustrates how the various components shown in FIG. 1 fit together. Note that fasteners are omitted from both FIGS. 1 and 2 for clarity. As indicated above, the lower annular surface 202 of the apparatus 100 is adapted to sit flush with the window surface of a processing tool view port. Also as indicated above, the outer flange edge 204 of the assembly 102 is adapted overhang the frame of the view port to facilitate attachment. The outer flange edge 204 includes holes to allow the assembly to be securely but removeably attached to the processing tool (e.g., via bolts).

Figure 3:
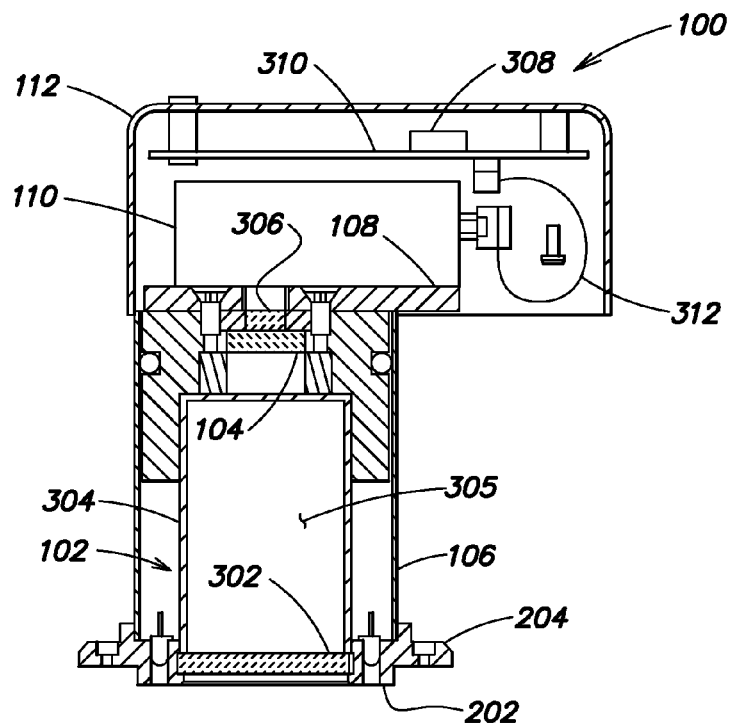
FIG. 3 depicts a cross-sectional view of the example apparatus embodiment of FIG. 2 taken along line 3-3.

Turning to FIG. 3, a cross-sectional view of the example apparatus 100 is depicted. The cross-section is taken along the line identified as 3—3 in FIG. 2. Note that the elements described above with respect to FIGS. 1 and 2 are labeled using the same reference numerals as in FIGS. 1 and 2. In FIG. 3 additional components of the optical energy supply base assembly 102 and the apparatus 100 are depicted. Specifically, a lower diffuser 302 is shown disposed within the inner diffusing tube 304. In addition, an optical bandpass filter 306 is shown disposed between the top diffuser 104 and the optical sensor assembly 110. Also, a controller 308 is depicted on a control circuit 310 which is supported by the shield housing 112. The control circuit 310 is coupled to the optical sensor assembly 110 via cabling 312.

As with the top diffuser 104, the lower diffuser 302 may be made of opal glass. In some embodiments, a thin layer of opal glass (e.g., approximately 0.05 to approximately 0.3 mm thick and preferably approximately 0.1 mm thick) may be fused to a thicker clear piece of glass (e.g., approximately 6 mm thick) to form the lower diffuser 302. In some embodiments, lower diffuser 302 may be disposed so that the opal glass layer is on the top surface of the lower diffuser 302, effectively further recessing the diffuser 302 into the inner diffusing tube 304.

The inner diffusing tube 304 may be formed from aluminum and includes an inner surface 305 coated with a randomly textured material to further scatter and randomize optical energy traveling through the tube 304. In some embodiments, the inner surface 305 of the inner diffusing tube 304 may be anodized to form a rough oxide layer. The thickness of the anodized layer may be approximately 32 microinches RMS.

The controller 308 and control circuit 310 may include a processor, logic circuitry, and/or any combination of hardware and software that is adapted to use the apparatus 100 to execute the methods of the present invention. For example, the controller 308 may include program code that is adapted to activate the optical energy supply base assembly 102 to illuminate a substrate in a processing tool in response to receiving a signal indicating the substrate is present. In some embodiments, the controller 308 may include program code that is adapted to use the optical energy supply base assembly 102 to detect the presence of a substrate in the processing tool. In some embodiments, the controller 308 may include program code that is adapted to send a signal to a host system or process tool controller indicating that a certain material has been detected on the substrate based upon receiving a signal from the optical sensor assembly 110 indicating the detection of a certain wavelength of optical energy received from the substrate. In some embodiments, the controller 308 may include program code that is adapted to calibrate the apparatus 100, to control the intensity of the optical energy sources, and/or to adjust the gain of the sensors in the optical sensor assembly 110. The controller 308 and control circuit 310 may also include interface ports, memory, clocks, power supplies, and other components to support operation of the controller 308.

Figure 4:
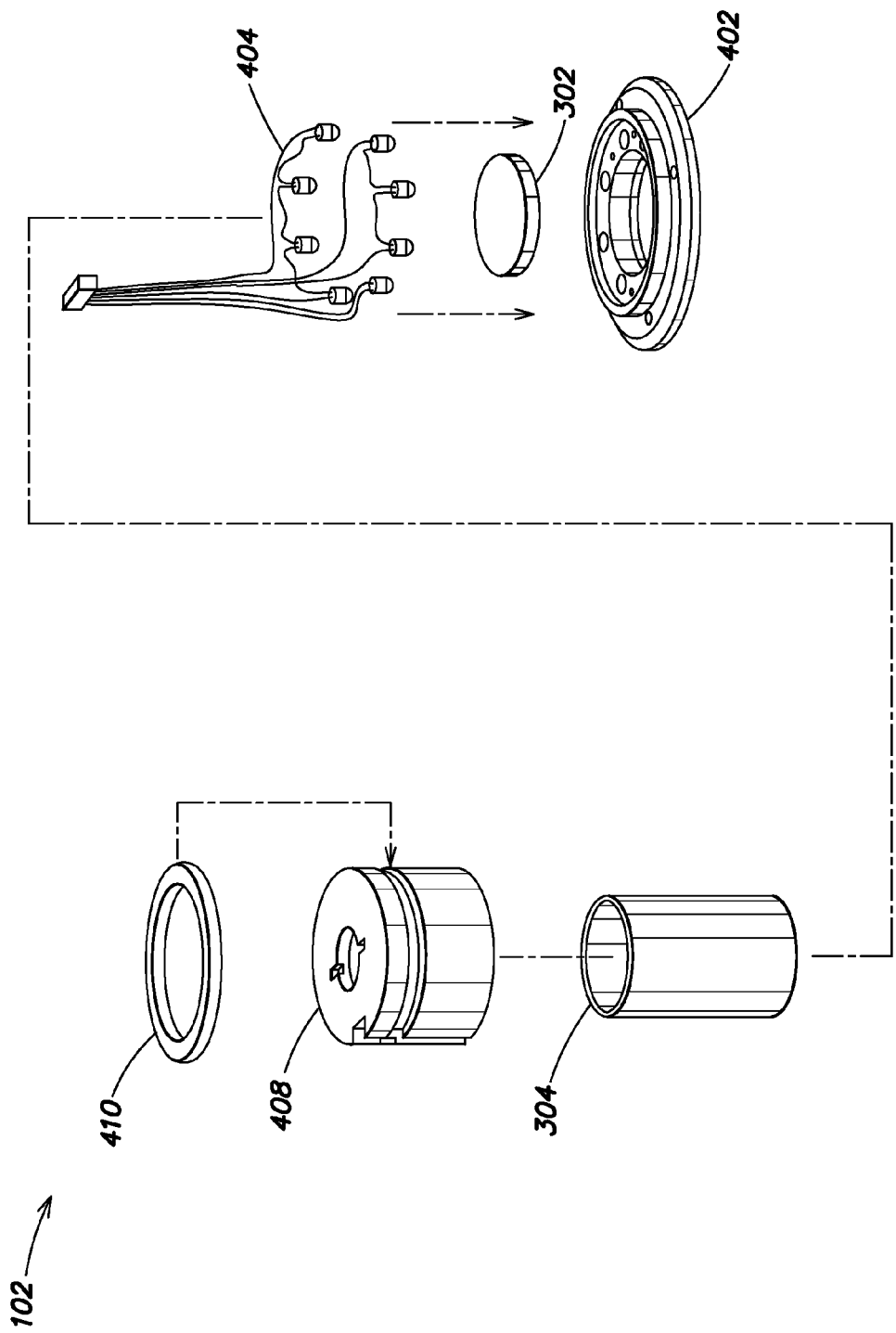
FIG. 4 depicts an exploded detailed perspective view of a portion of the example apparatus embodiment of FIG. 1.

Turning to FIG. 4, an exploded perspective view of the optical energy supply base assembly 102 is depicted. Note that fasteners are omitted for clarity. The optical energy supply base assembly 102 includes a base mounting member 402 that is adapted to support both the lower diffuser 302 and the optical energy source array 404, as well as to couple to a view port of a processing tool as described above. The optical energy supply base 102 further includes the inner diffusion tube 304 and an upper support member 408 which is adapted to hold the upper diffuser 104. The inner diffusion tube 304 is adapted to extend from the base mounting member 402 to the upper support member 408, thereby defining a path for the optical energy reflected from the substrate to flow to the optical sensor assembly 110. A spacer 410 (e.g., an O-ring) may be seated in a groove in the upper support member 408 to center the outer tube housing 106 around the optical energy supply base assembly 102 and to prevent relative movement between the two. The spacer 410 may also serve to secure and retain cabling between the optical energy supply base assembly 102 and the control circuit 310.

In addition to providing a means to easily, removeably, and securely couple the apparatus 100 to a processing tool view port, the base mounting member 402 includes a number of apertures to support both the lower diffuser 302 and the optical energy source array 404. In particular, the apertures include a plurality of approximately normal openings for LEDs or other energy sources and a pair of angled openings for a substrate presence detector emitter/sensor pair.

Figure 5:
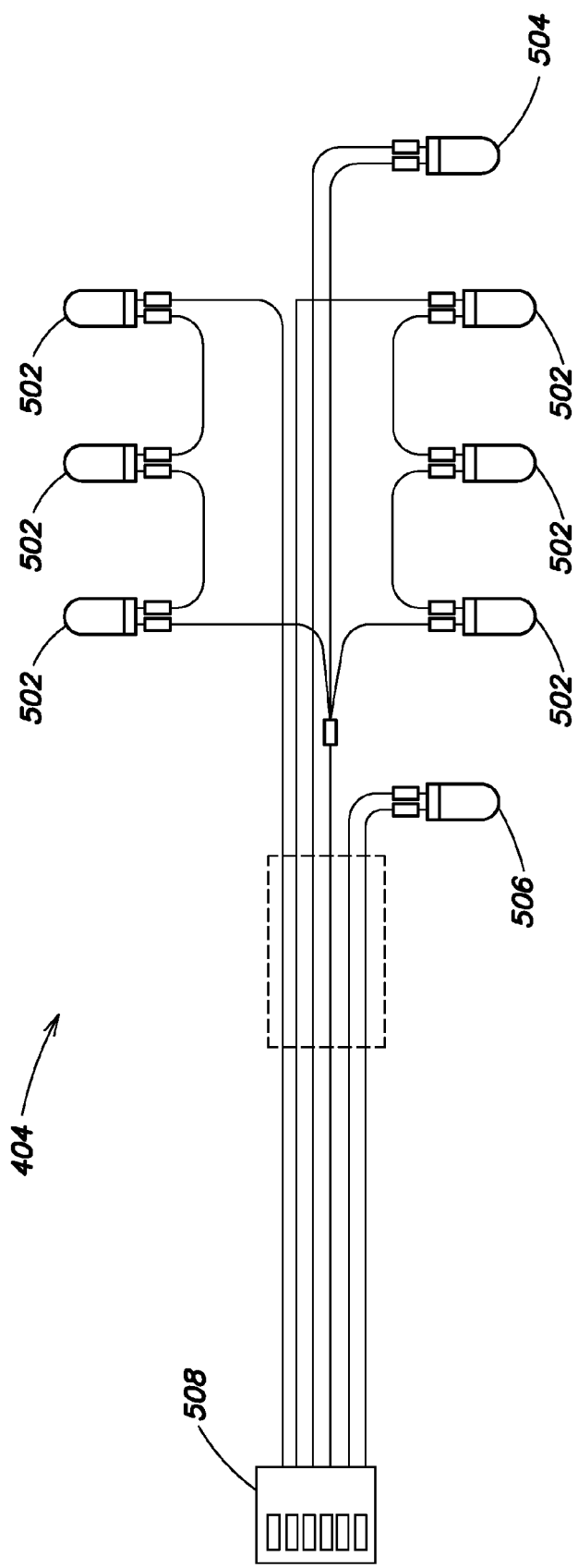
FIG. 5 depicts a detail view of an example embodiment of a component of FIG. 4.

Turning to FIG. 5, a diagram depicting the optical energy source array 404 is provided. The example array 404 shown includes six LEDs 502. However, any type and number of practicable sources may be used with a corresponding number of apertures in the base mounting member 402. As indicated above, various different types of sources may be used to generate optical spectrum energy in the range from infrared (about 1500 nm) through far ultraviolet (about 150 nm).

In some embodiments as shown in FIG. 5, the optical energy source array 404 may further include an emitter 504 and a sensor 506 which together may be used to form a substrate presence detector emitter/sensor pair. In addition to cabling, the optical energy source array 404 may further include a connector 508 adapted to connect to an interface port of the control circuit 310, thereby making manufacturing and servicing of the apparatus easier.

Figure 6:
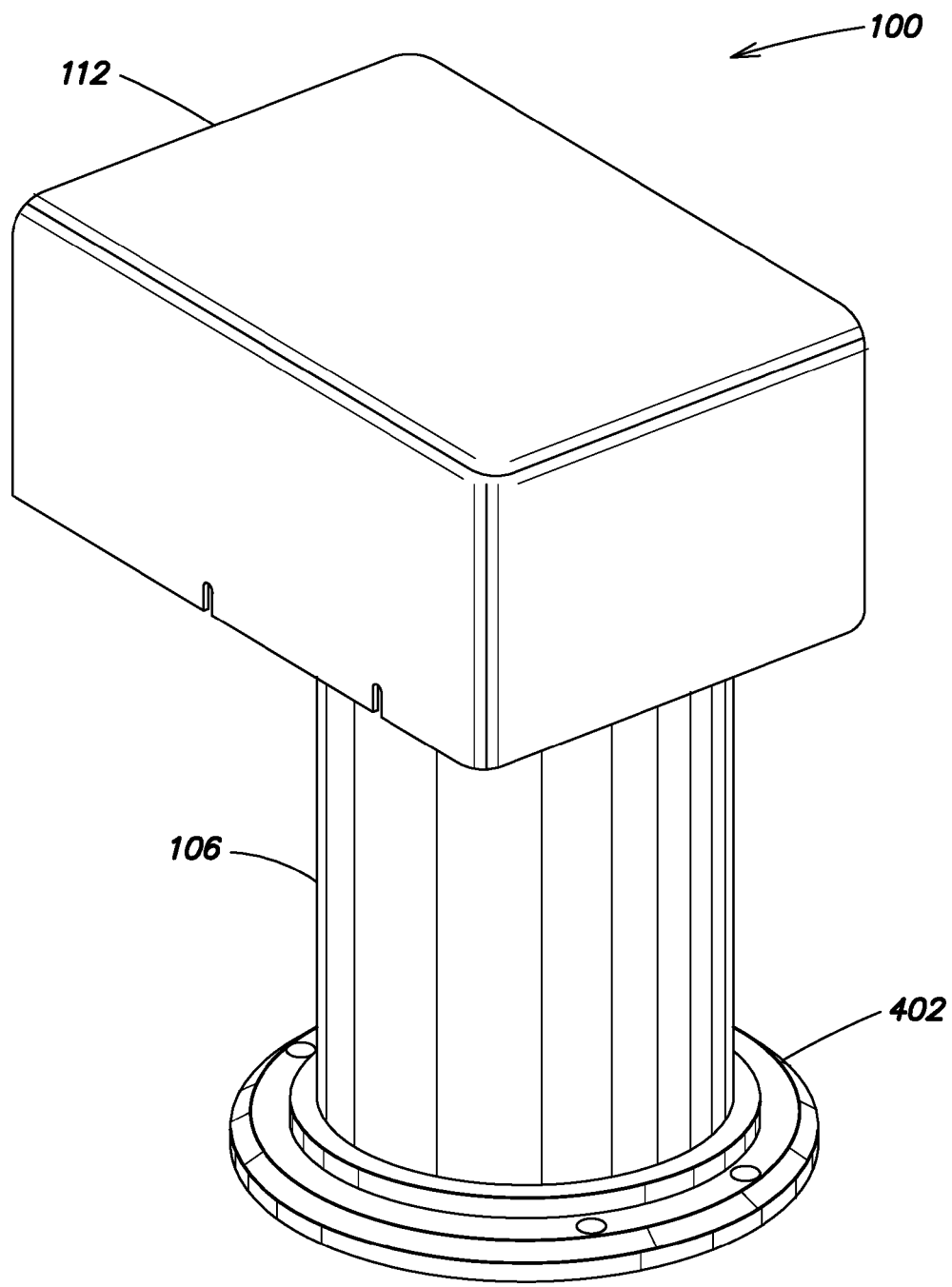
FIG. 6 depicts a front perspective view of the first example apparatus embodiment of the present invention.
Figure 7:
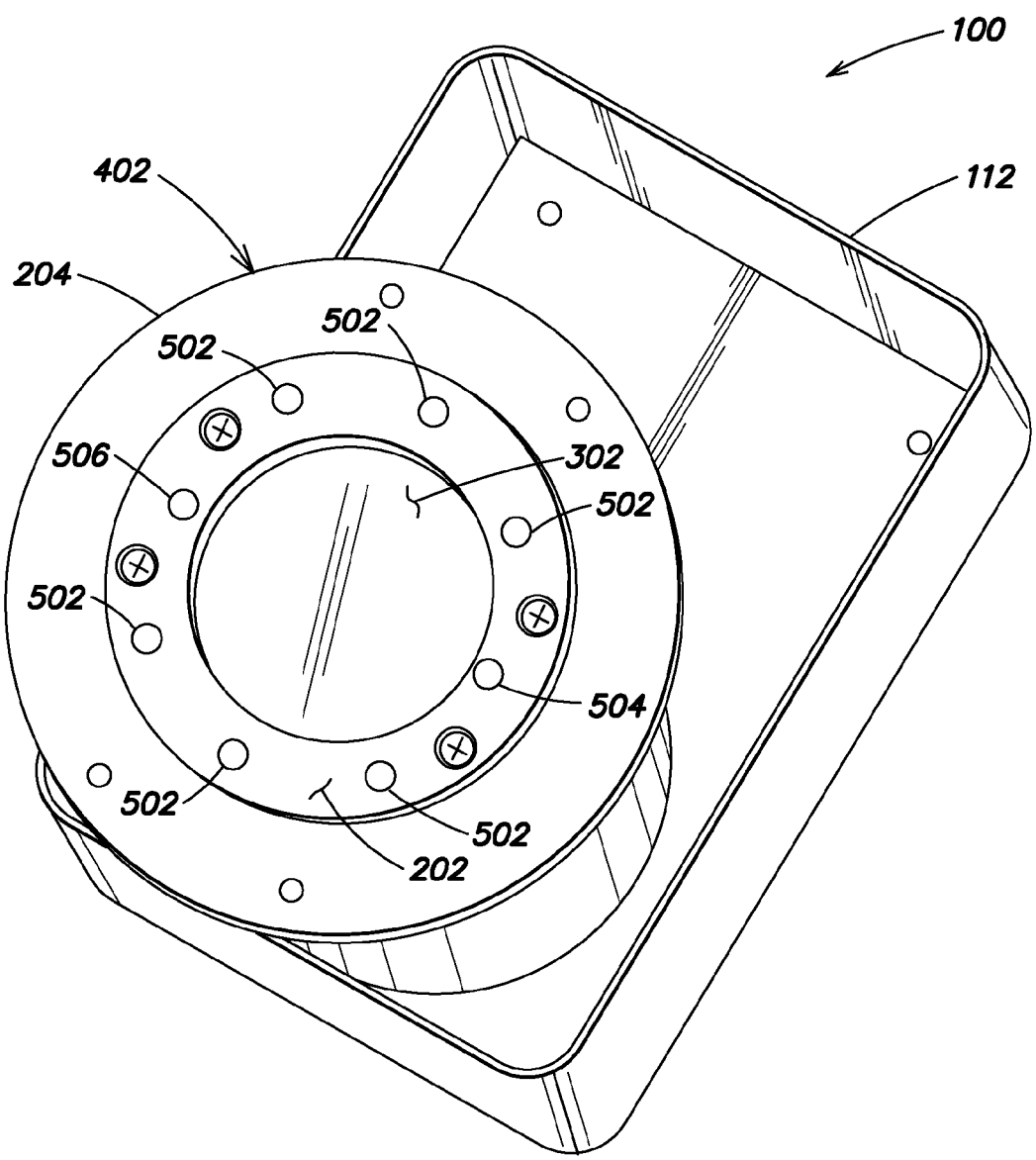
FIG. 7 depicts a bottom perspective view of an example apparatus embodiment of the present invention.

FIGS. 6 and 7 depict front and bottom perspective views, respectively, of the film detection apparatus 100. Note that the apparatus 100 may be adapted to have a low profile relative to the lid of a processing tool to which it is to be mounted. The desired vertical dimension largely defines the inner diffusion tube 304 length and as the length is increased, the amount of diffusion is increased, thereby improving the signal to noise ratio of the apparatus 100. Regarding FIG. 7, note the relative positions of the LEDs 502 disposed around the lower diffuser 302 to emit an even field of overlapping "field of view" cones onto the substrate. Also note the flat annular surface 202 adapted to sit flush on the view port window of a processing tool.

Figure 8:
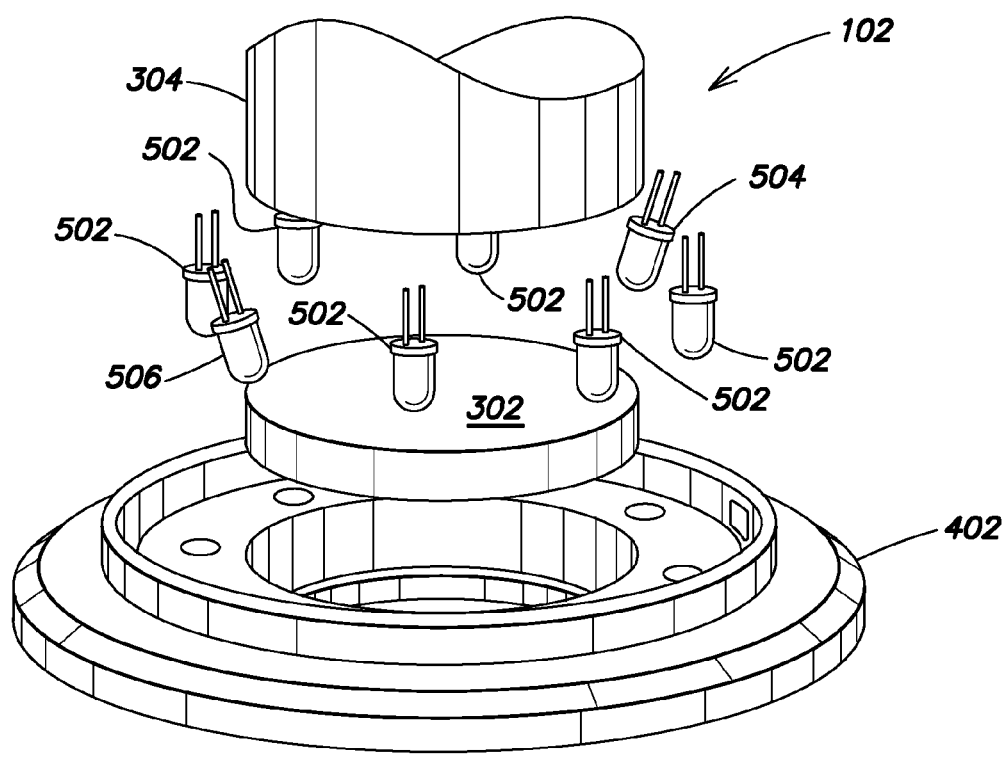
FIG. 8 depicts an exploded detailed perspective view of a portion of the example apparatus embodiment of FIG. 1.

Turning to FIG. 8, a detailed exploded perspective view of the lower portion of the optical energy supply base assembly 102 is provided. In particular, FIG. 8 depicts the relative positions of the lower diffuser 302, the inner diffuser tube 304, the LEDs 502, the emitter 504, and the sensor 506, and how each fits into or onto the base mounting member 402. The emitter 504 and the sensor 506 are shown angled at approximately 22.5 degrees to allow optical energy from the emitter 504 to reflect off a substrate and be received by the sensor 506. Other practicable angles may be used.

Figure 9:
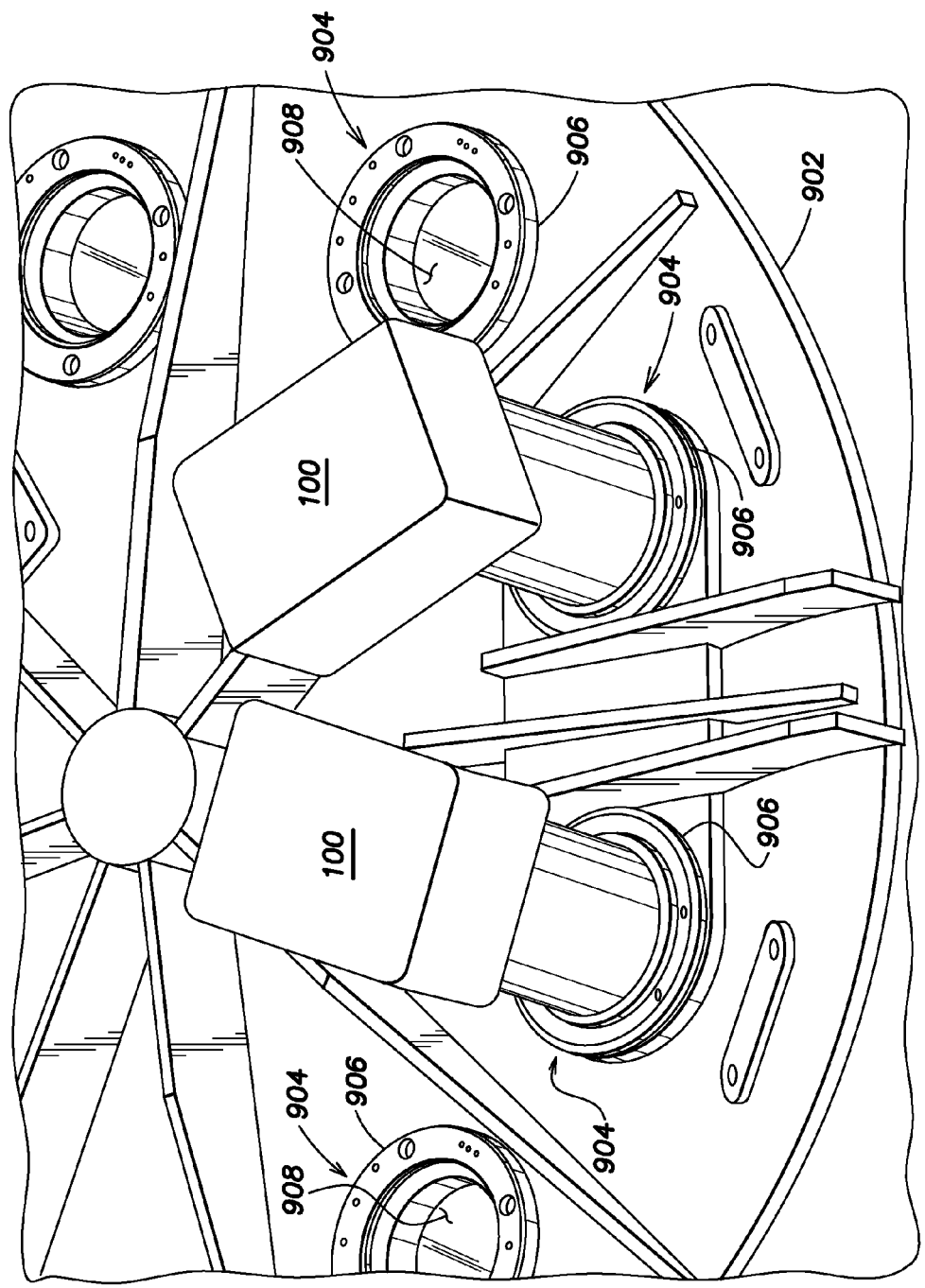
FIG. 9 depicts a perspective view of an example system embodiment of the present invention.

Turning to FIG. 9, a perspective view of an example system embodiment of the present invention is shown. Two film detection apparatuses 100 are shown coupled to the lid 902 of a part of a processing tool such as a transfer chamber. The lid 902 includes a plurality of view ports 904 which each include a frame 906 and a transparent window material 908. The apparatuses 100 of the present invention are shown bolted to the frames 906 of two view ports 904 with the flat annular surface 202 (FIG. 8) sitting flush on the transparent window material 908 seated within the frames 906. In the depicted configuration, ambient light is excluded from entering the apparatuses 100 except via the transparent window material 908.

Figure 10:
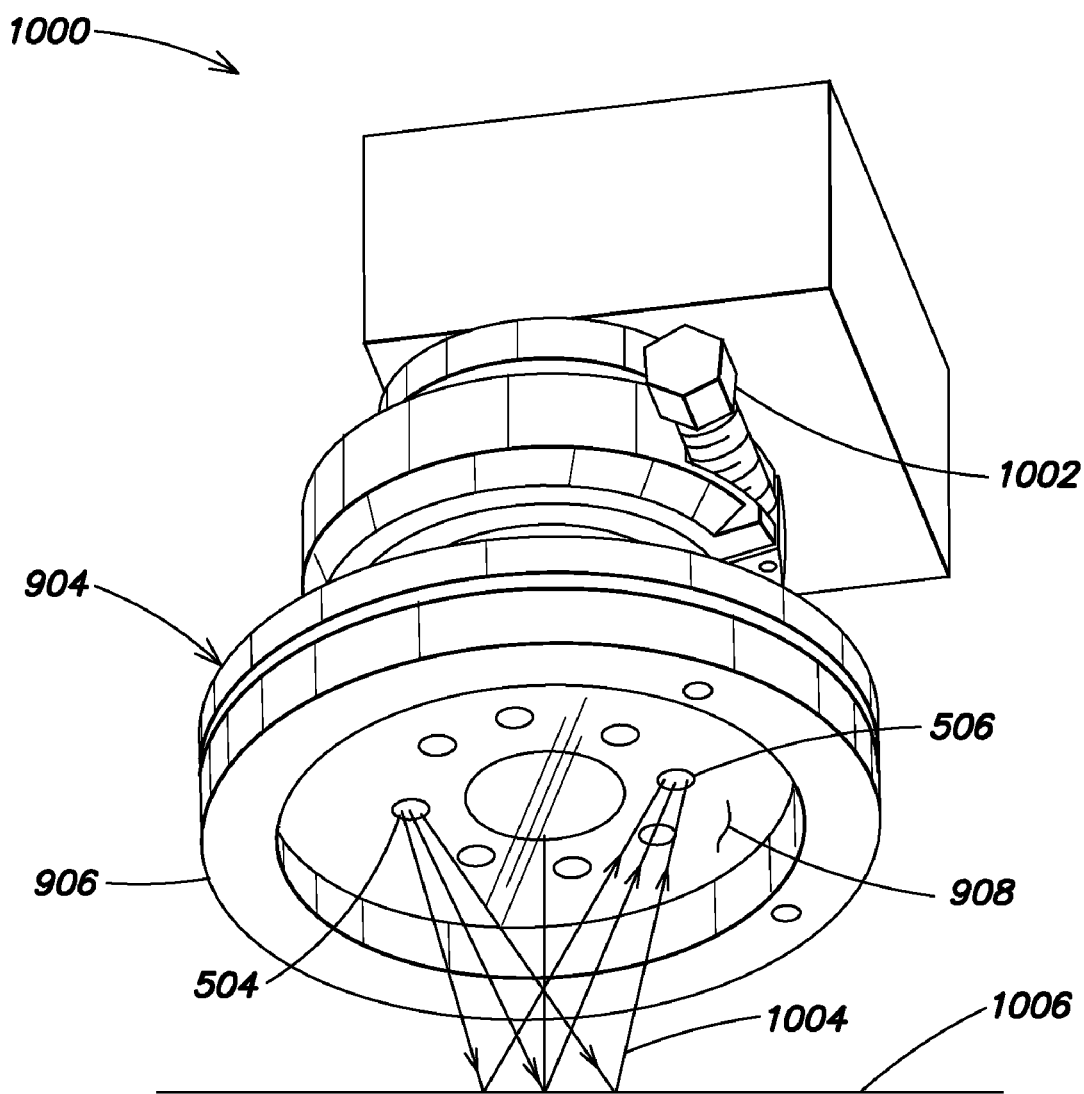
FIG. 10 depicts a partial bottom perspective view of an example system embodiment of the present invention.

Turning to FIG. 10, a second example embodiment of a film detection apparatus 1000 is depicted in perspective view. Note that this embodiment is similar to the example embodiment of FIG. 1 except the outer housing has a different shape and dimensions. This apparatus 1000 also includes an adjustment 1002 that allows the position of the upper diffuser to be altered. The apparatus 1000 is depicted coupled to a frame 906 of a view port 904 of a lid (omitted for clarity).

Optical energy rays 1004 are shown emanating from an emitter 504, passing through the transparent window material 908, reflecting off a substrate surface 1006, passing back through the transparent window material 908, and being received by a sensor 506. As shown, when a substrate is present, the optical energy rays 1004 reflect off the substrate surface 1006 and the substrate is detected. If the substrate is not present, the rays 1004 are not reflected back to the sensor 506, and the apparatus 1000 is able to determine that a substrate is not present.

Figure 11:
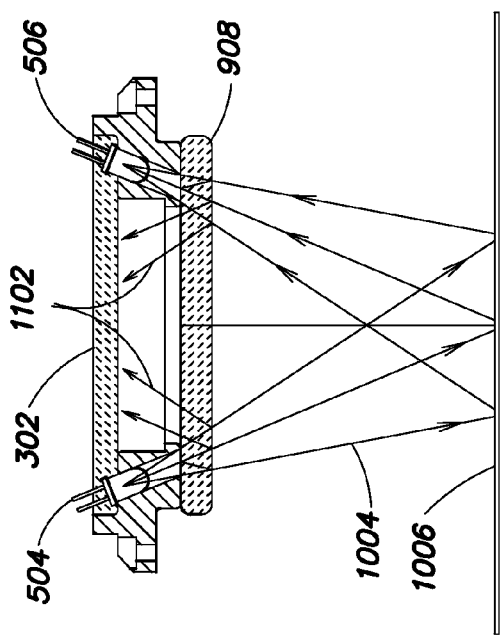
FIG. 11 depicts an example embodiment of the apparatus of the present invention in operation performing a first method of the present invention.

Turning to FIG. 11, a cross-sectional view illustrating the ray trace shown in perspective in FIG. 10 is provided. As with FIG. 10, optical energy rays 1004 are shown emanating from an emitter 504, passing through the transparent window material 908, reflecting off a substrate surface 1006, passing back through the transparent window material 908, and being received by a sensor 506. As shown, when a substrate is present, the optical energy rays 1004 reflect off the substrate surface 1006 and the substrate is detected. If the substrate is not present, the rays 1004 are not reflected back to the sensor 506, and the apparatus 1000 is able to determine that a substrate is not present.

Note that, although not a concern in the depicted method of determining a substrate presence, some rays 1102 are reflected off the transparent window material 908 toward the lower diffuser 302. Thus, when the present invention is used to detect the presence of a film on a substrate, the emitter 504 is preferably turned off.

Figure 12:
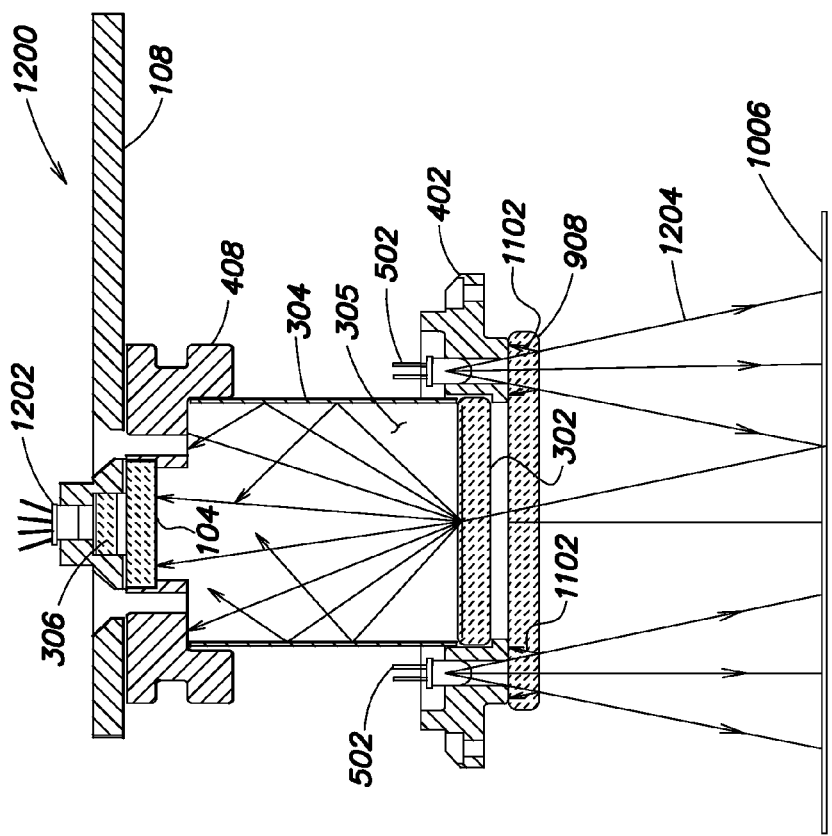
FIG. 12 depicts an example embodiment of the apparatus of the present invention in operation performing a second method of the present invention.

Turning to FIG. 12, a ray trace drawing illustrating some paths of optical spectrum energy is provided. The ray trace is shown using a cross-sectional view of a third example embodiment of a film detection apparatus 1200. The different features of the example apparatus 1200 of FIG. 12 are described in more detail below with respect to FIG. 13.

The apparatus 1200 causes rays 1204 to emanate from LEDs 502. The rays 1204 form an even, overlapping pattern of circular fields of energy that are reflected by the substrate 1006 back toward the lower diffuser 302. The wavelengths of the LEDs 502 are selected to generate energy rays 1204 that are reflected by the material that is to be detected better than other materials. Thus, if the target detection material is present, more energy is reflected. In operation, the apparatus of the present invention detects differences in the amount of optical spectrum energy reflected by the substrate. Preferably, wavelengths are selected that have an approximately 20% intensity difference when reflecting off of a target detection material versus other non-target detection materials. Other percentage differences may be used to determine the presence of the target detection material.

Because the electronic devices on the substrate reflect energy unevenly due to their geometry, imaging effects, and other reasons, in addition to the particular materials present, the present invention uses diffusion to reduce the influence of geometry, imaging effects, and the other reasons while maintaining the amount of energy reflected by the particular materials present. In other words, diffusion is used to reduce the influence of geometry, imaging effects, and the other reasons, without effecting the relative amount of energy that is reflected by the films on the substrate. According to embodiments of the present invention, accurate, repeatable and reliable film detection may be achieved with a signal to noise ratio of less than approximately 2% and preferably less than approximately 1%.

After the rays 1204 reflect off of the substrate 1006, the rays 1102 pass through the transparent window material 908 of the view port toward the lower diffuser 302. Note that rays 1102 reflected off the transparent window material 908 are blocked from reaching the lower diffuser 302 by the base mounting member 402. In fact, the geometry of the present invention is designed so that only rays 1204 reflecting off of the substrate 1006 may reach the lower diffuser 302 and ultimately the sensor 1202.

Embodiments of the present invention use three levels of diffusion. The rays 1204 are first diffused through the lower diffuser 302, then they are further randomized by the inner surface 305 of the inner diffusion tube 304, and finally, they pass through the upper diffuser 104. In some embodiments, an optical bandpass or other filter 306 is used to filter certain wavelengths as described above. The rays 1204 then arrive at the sensor 1202 and the presence of the target detection material is indicated by the relative amount of energy detected at a predefined wavelength associated with the target detection material.

Figure 13:
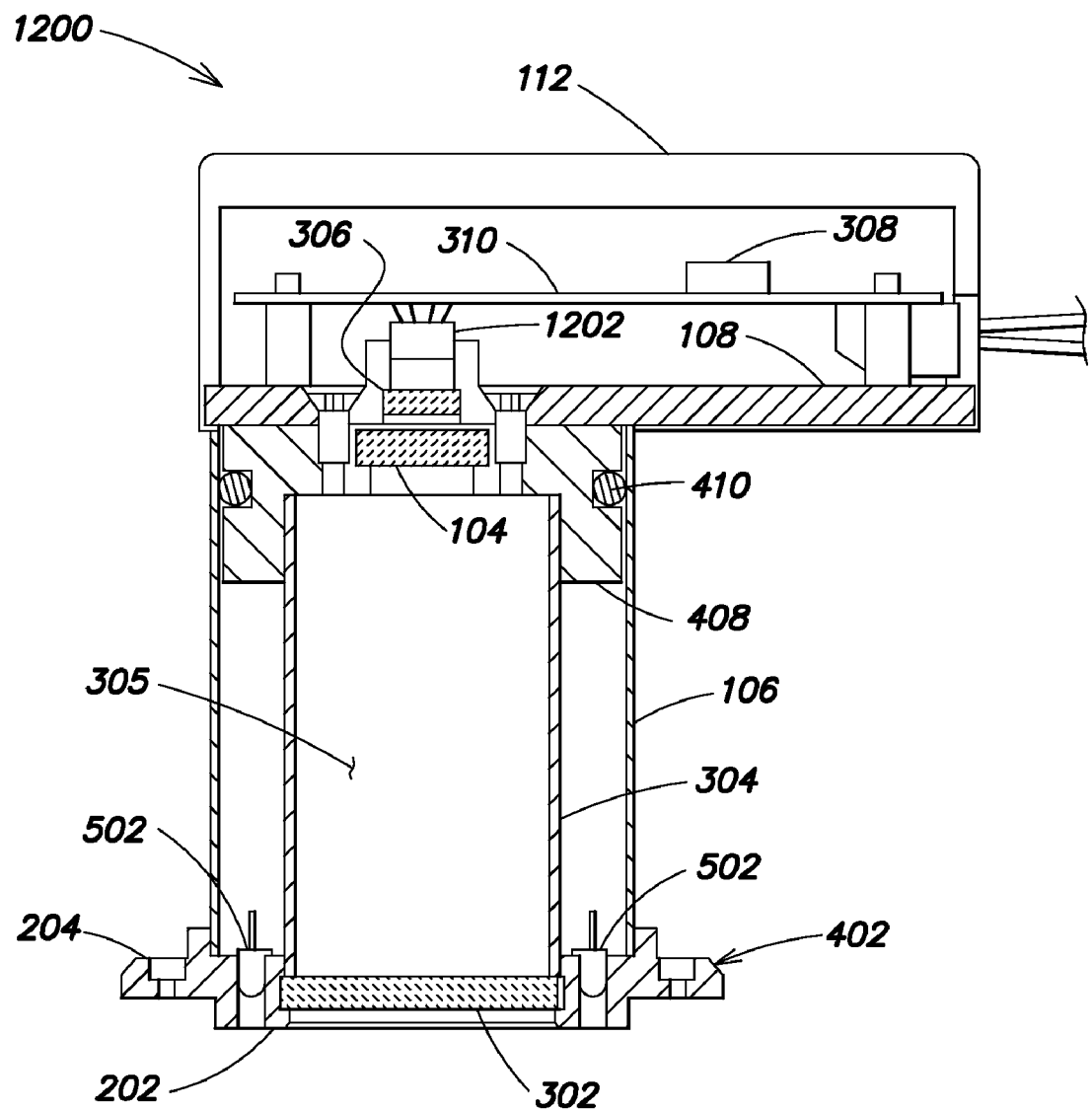
FIG. 13 depicts a front perspective view of a second example apparatus embodiment of the present invention.

Turning to FIG. 13, a more detailed cross-sectional view of the third example embodiment of a film detection apparatus 1200 is depicted. The elements corresponding to the features described above are identified with the same reference numerals used in the description in the embodiments described above. The primary difference between the film detection apparatus 1200 and the film detection apparatus 100 is the elimination of the separate optical sensor assembly 110 from the film detection apparatus 1200. Instead, a sensor 1202 is integrated into the control circuit 310. This difference significantly further reduces the cost and complexity of the present invention.

Note that the example embodiments described herein are only possible examples of substrate film sensor configurations and that variants of them are within the scope of the basic concept as conceived. In other words, the foregoing description discloses only exemplary embodiments of the invention. Modifications of the above disclosed apparatus and method which fall within the scope of the invention will be readily apparent to those of ordinary skill in the art. Accordingly, while the present invention has been disclosed in connection with specific exemplary embodiments thereof, it should be understood that other embodiments may fall within the spirit and scope of the invention, as defined by the following claims.

The invention claimed is:

1. An apparatus for detecting a film in an electronic device in an electronic device processing tool comprising:
   a mounting member adapted to couple the apparatus to a view port of the electronic device processing tool;
   an optical energy source disposed within the mounting member and adapted to illuminate the electronic device within the electronic device processing tool with a multiplicity of optical wavelengths which are simultaneous, sequenced, or selectively enabled;
   an optical system adapted to pass wavelengths indicative of a presence of the film;
   an optical detector positioned to receive optical energy reflected from the substrate and passing through the optical system adapted to detect a presence or absence of the film;
   an additional optical energy source; and
   an additional optical detector disposed to receive optical energy reflected from the substrate,
   wherein the additional optical energy source and optical detector are adapted to detect a presence or absence of the substrate within the electronic device processing tool.

2. The apparatus of claim 1 wherein the mounting member includes an aperture disposed to support the optical energy source so that only optical energy reflected from the substrate reaches the optical detector.

3. The apparatus of claim 1 further including a housing coupled to the mounting member and adapted to exclude optical energy from reaching the optical detector that is not reflected from the substrate.

4. The apparatus of claim 1 wherein the optical system includes a diffuser.

5. The apparatus of claim 1 wherein the optical system includes a plurality of diffusers and a filter.

6. The apparatus of claim 5 wherein the plurality of diffusers includes a diffuser disposed at either end of a diffusion tube.

7. A system for detecting a film in an electronic device comprising:
   an electronic device processing tool;
   a mounting member adapted to couple to a view port of the electronic device processing tool;
   an optical energy source disposed within the mounting member and adapted to illuminate the electronic device within the electronic device processing tool with a multiplicity of optical wavelengths which are simultaneous, sequenced, or selectively enabled;
   an optical system coupled to the mounting member and adapted to pass wavelengths indicative of a presence of the film;
   an optical detector positioned to receive optical energy reflected from the substrate and passing through the optical system adapted to detect a presence or absence of the film;
   an additional optical energy source; and
   an additional optical detector disposed to receive optical energy reflected from the substrate,
   wherein the additional optical energy source and optical detector are adapted to detect a presence or absence of the substrate within the electronic device processing tool.

8. The system of claim 7 wherein the mounting member includes an aperture disposed to support the optical energy source so that only optical energy reflected from the substrate reaches the optical detector.

9. The system of claim 7 further including a housing coupled to the mounting member and adapted to exclude optical energy from reaching the optical detector that is not reflected from the substrate.

10. The system of claim 7 wherein the optical system includes a diffuser.

11. The system of claim 7 wherein the optical system includes a plurality of diffusers and a filter.

12. The system of claim 11 wherein the plurality of diffusers includes a diffuser disposed at either end of a diffusion tube.

13. A method of detecting a film in an electronic device disposed an electronic device processing tool, the method comprising:
   coupling a mounting member of a film detection apparatus to a view port of the electronic device processing tool;
   illuminating the electronic device within the electronic device processing tool using an optical energy source disposed within the mounting member with a multiplicity of optical wavelengths which are simultaneous, sequenced, or selectively enabled;

passing wavelengths indicative of a presence of the film via an optical system coupled to the mounting member;

receiving optical energy reflected from the substrate;

detecting a presence or absence of the film based on the received optical energy using an optical detector;

illuminating the substrate using an additional optical energy source;

receiving optical energy with an additional optical detector disposed to receive optical energy reflected from the substrate; and determining the presence or absence of the substrate within the electronic device processing tool based on the optical energy reflected from the substrate.

14. The method of claim 13 further including supporting the optical energy source using the mounting member so that only optical energy reflected from the substrate reaches the optical detector.

15. The method of claim 13 further including excluding optical energy from reaching the optical detector that is not reflected from the substrate using a housing coupled to the mounting member.

16. The method of claim 13 wherein passing wavelengths indicative of a presence of the film includes passing the optical energy through a diffuser.

17. The method of claim 13 wherein passing wavelengths indicative of a presence of the film includes passing the optical energy through a plurality of diffusers and a filter.

18. The method of claim 17 wherein passing the optical energy through a plurality of diffusers includes passing the optical energy through a diffuser disposed at either end of a diffusion tube.

* * * * *